US012336688B2

(12) United States Patent
Hedemann et al.

(10) Patent No.: US 12,336,688 B2
(45) Date of Patent: Jun. 24, 2025

(54) OUTER SHAFT FOR AN ENDOSCOPE AND ENDOSCOPE SYSTEM

(71) Applicant: KARL STORZ SE & Co. KG, Tuttlingen (DE)

(72) Inventors: Lars Hedemann, Tuttlingen (DE); Andreas Heni, Tuttlingen (DE)

(73) Assignee: KARL STORZ SE & Co. KG, Tuttlingen (DE)

( * ) Notice: Subject to any disclaimer, the term of this patent is extended or adjusted under 35 U.S.C. 154(b) by 387 days.

(21) Appl. No.: 17/948,704

(22) Filed: Sep. 20, 2022

(65) Prior Publication Data

US 2023/0087086 A1    Mar. 23, 2023

(30) Foreign Application Priority Data

Sep. 21, 2021   (DE) .......................... 102021124453.6

(51) Int. Cl.
*A61B 1/018* (2006.01)
*A61B 1/00* (2006.01)
*G02B 23/24* (2006.01)

(52) U.S. Cl.
CPC .......... *A61B 1/018* (2013.01); *A61B 1/00135* (2013.01); *G02B 23/243* (2013.01); *A61B 1/00112* (2013.01)

(58) Field of Classification Search
CPC . A61B 1/018; A61B 1/00112; A61B 1/00121; A61B 1/00135; A61B 1/00119;

(Continued)

(56) References Cited

U.S. PATENT DOCUMENTS 4,685,450 A * 8/1987 Collins ..................... A61B 1/04
396/17
5,287,845 A * 2/1994 Faul ......................... A61B 1/12
600/156

(Continued)

FOREIGN PATENT DOCUMENTS

DE      10 2017 103 545 A1    8/2018
EP         1542579 B1          10/2010

(Continued)

OTHER PUBLICATIONS

May 12, 2022—(DE) Examination Report—App. No. 10 2021 124 453.6.
Feb. 13, 2023—(EP) Office Action—App. No. EP 22 19 3396.3.

*Primary Examiner* — John P Leubecker
*Assistant Examiner* — Li-Ting Song
(74) *Attorney, Agent, or Firm* — Banner & Witcoff, Ltd.

(57) ABSTRACT

An outer shaft for receiving a shaft of an endoscope comprises a proximal end region for receiving a proximal end region of the shaft of the endoscope, a sealing surface for resting on a corresponding sealing surface of the endoscope for locally fluid-tight sealing of an intermediate space between outer shaft and shaft of the endoscope and a radially inwardly protruding cleat in the proximal end region for proximally engaging behind a radially outwardly protruding cleat on the proximal end region of the shaft of the endoscope. The radially inwardly protruding cleat is provided on a section of the proximal end region of the outer shaft that is elastically deformable in the axial direction of the outer shaft.

11 Claims, 4 Drawing Sheets

(58) Field of Classification Search
CPC . A61B 1/00147; A61B 1/00128; A61M 39/10
See application file for complete search history.

(56) References Cited

U.S. PATENT DOCUMENTS

| | | | |
|---|---|---|---|
| 5,575,756 A | | 11/1996 | Karasawa et al. |
| 5,709,698 A | | 1/1998 | Adams et al. |
| 6,126,359 A | * | 10/2000 | Dittrich .................... B25G 3/04 |
| | | | 403/325 |
| 11,337,601 B2 | * | 5/2022 | Rehbein ............. A61B 1/00128 |
| 2005/0085692 A1 | | 4/2005 | Kiehn et al. |
| 2011/0004062 A1 | * | 1/2011 | Asai ................... A61B 1/00137 |
| | | | 600/114 |
| 2014/0336688 A1 | * | 11/2014 | Bacher ................. A61B 46/10 |
| | | | 606/191 |
| 2015/0029816 A1 | * | 1/2015 | Beyer ................ B01F 35/7176 |
| | | | 366/167.1 |
| 2015/0173840 A1 | * | 6/2015 | Lohmeier .............. A61B 17/00 |
| | | | 606/130 |
| 2017/0014161 A1 | * | 1/2017 | Gemmer ............... A61M 29/00 |
| 2020/0222055 A1 | * | 7/2020 | Ibrahim ................ A61B 1/018 |
| 2022/0312935 A1 | * | 10/2022 | Del Din ............. A45D 40/0068 |
| 2023/0124469 A1 | * | 4/2023 | Jackl ........................ B60S 1/02 |
| | | | 359/507 |

FOREIGN PATENT DOCUMENTS

| | | | |
|---|---|---|---|
| EP | 2552293 B1 | 1/2015 | |
| WO | 2014158574 A1 | 10/2014 | |
| WO | 2018/165365 A2 | 9/2018 | |
| WO | 2019/126683 A1 | 6/2019 | |

* cited by examiner

OUTER SHAFT FOR AN ENDOSCOPE AND ENDOSCOPE SYSTEM

This application claims the benefit of and priority to DE 10 2021 124 453.6, entitled "Outer Shaft for an Endoscope and Endoscope System" filed Sep. 21, 2021, which is hereby incorporated by reference in its entirety for any and all non-limiting purposes.

The present invention relates to an outer shaft for an endoscope and to an endoscope system with an outer shaft and an endoscope.

Medical instruments with long thin shafts are described in EP 1 542 579 B1, EP 2 552 293 B1, WO 2018/165365 A2 and WO 2019/126683 A1 and, in addition to devices for capturing and transmitting images, they also have one or a plurality of fluid channels to conduct flushing fluid or to suction a fluid from a situs. In order to simplify or ensure complete cleaning and sterilization, an outer shaft can be positioned over the shaft of an endoscope. Between outer shaft and shaft of the endoscope, there remains a sheath-shaped fluid channel with in particular substantially circular cross-section, through which a flushing fluid is conducted to the distal end or a fluid can be suctioned from the distal end of the arrangement. The endoscope has, in the transition region between the proximal end of the shaft and the distal end of the handling device, for example convex regions, on which the proximal end of the outer shaft can be fastened. Displaceable, pivotable or rotatable bolts on the proximal end of the outer shaft enable a detachable mechanical connection.

An object of the present invention is to provide an improved outer shaft for an endoscope and an improved endoscope system.

This object is achieved by the subject matters of the independent claims.

Further embodiments are defined in the dependent claims.

An outer shaft for receiving a shaft of an endoscope comprises a proximal end region for receiving a proximal end region of the shaft of the endoscope, a sealing surface for resting on a corresponding sealing surface of the endoscope for locally fluid-tight sealing of an intermediate space between outer shaft and shaft of the endoscope and a radially inwardly protruding cleat in the proximal end region, for proximally engaging behind a radially outwardly protruding cleat on the proximal end region of the shaft of the endoscope, wherein the radially inwardly protruding cleat is provided on a section of the proximal end region of the outer shaft that is elastically deformable in the axial direction of the outer shaft.

The outer shaft is provided and designed for the exclusive use with an endoscope of a predetermined design or a design made up of a predetermined group of designs both constructively through its length, the cross-section of its lumen and the geometry of the sealing surface and of the radially inwardly protruding cleat as well as legally through its specific approval under medical devices law. In this case, the design or the group of designs is clearly designated in the approval under medical devices law.

The outer shaft can be provided to form an endoscope system made of the outer shaft and an endoscope for different medical procedures. Both the outer shaft and the shaft of the endoscope can be designed to be rigid and straight or curved, or flexible in sections or in its entirety.

The intermediate space between outer shaft and shaft of the endoscope has in particular at least in sections a ring-shaped, for example, circular cross-section and extends up to a distal end of the arrangement of outer shaft and shaft of the endoscope. The intermediate space can be provided and designed to conduct a flushing fluid to this distal end and to suction a fluid therefrom. The intermediate space between outer shaft and shaft of the endoscope can have in the proximal end region an extended cross-section and merge into a, for example, radially arranged fluid connection.

The sealing surface on the outer shaft and the corresponding sealing surface of the endoscope, when they rest on one another, seal the proximal end of the intermediate space between outer shaft and shaft of the endoscope in a fluid-tight manner. To this end, the sealing surface of the outer shaft is in particular a concave cone shape and the sealing surface of the endoscope is a convex cone shape, wherein diameters and opening angles are identical or similar.

The radially inwardly protruding cleat in the proximal end region of the outer shaft and the radially outwardly protruding cleat on the proximal end region of the shaft of the endoscope are each designed in particular as straight or curved webs with trapezoidal or rectangular cross-sections. During the intended use of the outer shaft, in which the sealing surface on the outer shaft is pressed against the sealing surface of the endoscope, the radially inwardly protruding cleat in the proximal end region of the outer shaft is arranged proximally to the radially outwardly protruding cleat on the proximal end region of the shaft of the endoscope.

While the outer shaft is fastened to the endoscope, the elastically deformable section is elastically deformed in the proximal direction. The resulting elastic restoring force presses a distally oriented surface region of the radially inwardly protruding cleat of the outer shaft against a proximally oriented surface region of the radially outwardly protruding cleat on the proximal end region of the shaft. As a result, the sealing surface on the outer shaft is pressed against the sealing surface of the endoscope at the same time.

The outer shaft has a particularly simple mechanical structure with the radially inwardly protruding cleat on the elastically deformable section of the proximal end region of the outer shaft. In particular, movable parts are not required for the connection of outer shaft and endoscope. This can enable cost-effective manufacture and significant mechanical robustness. In particular, the outer shaft or at least the proximal end region of the outer shaft, including the elastically deformable section and the radially inwardly protruding cleat, can be manufactured monolithically, for example as a cast part, in particular as an injection-molded part.

In the case of an outer shaft, as it is described here, the elastically deformable section of the proximal end region has in particular substantially the shape of a straight or curved bar which is connected at one end or at both its ends to the other proximal end region.

The elastically deformable section has in particular the shape of a bar, which is parallel or substantially parallel to a plane orthogonal to the longitudinal axis of the outer shaft. For example, the elastically deformable section is designed as a bar arranged in the direction of the circumference of the proximal end region and curved following the contour of the proximal end region.

The elastically deformable section is in particular elastically bent and/or twisted when fastening the outer shaft onto the endoscope.

In the case of an outer shaft, as it is described here, in particular both ends of the elastically deformable section are connected to the other proximal end region of the outer shaft, wherein the elastically deformable section has, close to its ends, an increased elastic flexibility.

In the case of an outer shaft, as it is described here, the elastically deformable section has, in particular close to both its ends, reduced cross-sections.

The elastically deformable section is, in particular close to its ends, elastically deformed in a first direction and, between its ends, in a second opposing direction.

In the case of an outer shaft, as it is described here, the elastically deformable section is separated from the other proximal end region in particular by a slot running substantially in the circumferential direction of the proximal end region of the outer shaft.

The slot can have a constant width or a width that varies in its longitudinal direction. The ends of the slot define the ends of the elastically deformable section.

Instead of a slot, a groove can be provided, which significantly reduces the wall thickness of the proximal end region locally and therefore increases the elasticity of the proximal end region locally. The groove proceeds in particular from the inner side of the proximal end region.

In the case of an outer shaft, as it is described here, the proximal end region of the outer shaft is in particular substantially funnel-shaped or cup-shaped and open proximally.

The proximal edge of the proximal end region of the outer shaft lies in particular in a plane orthogonal to the longitudinal axis of the outer shaft. The radially inwardly protruding cleat protrudes in particular into the hollow space defined by the proximal end region in a funnel-shaped or cup-shaped manner. The radially inwardly protruding cleat is in particular arranged close to the proximal edge or directly adjacent to the proximal edge of the proximal end region of the outer shaft.

In the case of an outer shaft, as it is described here, the proximal end region has in particular a recess, which runs in the axial direction and is open radially, for passing through the radially outwardly protruding cleat on the proximal end region of the shaft of the endoscope while the shaft of the endoscope is inserted axially into the outer shaft, wherein the radially inwardly protruding cleat of the outer shaft is designed and arranged in order to adopt in a sliding manner a position proximal to the radially outwardly protruding cleat of the endoscope during a rotation of the outer shaft, which follows the axial insertion, relative to the endoscope on the radially outwardly protruding cleat of the endoscope.

The recess is in particular designed as a groove, which is wide in the circumferential direction, flat in the radial direction and short in the axial direction. The cross-section of the recess running in the axial direction and open radially inwardly is in particular adapted to the cross-section of the radially outwardly protruding cleat of the endoscope, wherein the cross-sections are each related to a section plane orthogonal to the longitudinal axis of the outer shaft and of the shaft of the endoscope. During the rotation of the outer shaft relative to the endoscope, which follows the axial insertion, the elastically deformable section is elastically deformed.

An outer shaft, as it is described here, in particular also comprises a ramp surface on the cleat of the outer shaft to generate a force deforming the elastically deformable section in the axial direction of the outer shaft when the outer shaft is rotated relative to the endoscope.

The ramp surface runs substantially in the circumferential direction, but is inclined with respect to a plane orthogonal to the longitudinal axis of the outer shaft. The angle between the ramp surface and the plane orthogonal to the longitudinal axis of the outer shaft is dependent on the elasticity of the elastically deformable section and on the resulting restoring force and therefore in particular on the geometry and the material of the elastically deformable section. The angle is in particular in the range of 5° to 40° or in the range of 10° to 30°. During the rotation of the outer shaft relative to the endoscope, the radially outwardly protruding cleat of the endoscope slides on the ramp surface of the radially inwardly protruding cleat of the outer shaft.

An outer shaft, as it is described here, in particular also comprises a plateau surface merging into the ramp surface on the cleat of the outer shaft.

During the intended use, the radially outwardly protruding cleat of the endoscope rests in particular on the plateau surface on the cleat of the outer shaft.

In the case of an outer shaft, as it is described here, in a configuration in which the outer shaft is connected to the endoscope in the intended manner, the elastic restoring force of the elastically deformable section presses the radially inwardly protruding cleat of the outer shaft in the axial direction against the radially outwardly protruding cleat of the endoscope and the sealing surface of the outer shaft against the corresponding sealing surface of the endoscope and thus locks the outer shaft in regard to a rotation relative to the endoscope in a frictionally-engaging manner.

The frictional engagement is dependent both on the tribological properties and on the geometric properties, namely sizes and inclinations of the surface regions resting on one another. Frictional engagement can result between the involved surface regions of the radially inwardly protruding cleat of the outer shaft and the radially outwardly protruding cleat of the endoscope and, due to the conicity, in particular between the sealing surface of the outer shaft and of the corresponding sealing surface of the endoscope.

In the case of an outer shaft, as it is described here, there is no latching or other partial or complete positive locking of the rotary position of the outer shaft relative to the endoscope.

The frictional engagement between the concavely cone-shaped sealing surface and the convexly cone-shaped corresponding sealing surface of the endoscope can in particular be strong enough to render latching or other partial or complete positive locking superfluous.

Alternatively or additionally, latching or other partial or complete positive locking can be provided. This may be required or be advantageous depending on the tribological properties of the material used and their surfaces.

In the case of an outer shaft, as it is described here, the outer shaft, including the radially inwardly protruding cleat, is in particular made of plastic and is intended and designed for single use.

The outer shaft is in particular not autoclavable and therefore also not or not readily reusable. The outer shaft is, however, in particular intended and designed for use with a reusable endoscope, i.e. with an endoscope that can be used multiple times. Alternatively, the outer shaft can be provided and designed to be used with a single-use endoscope, i.e. an endoscope which must be disposed of after one use and is not intended for reconditioning or reuse.

In the case of an outer shaft, as it is described here, in particular on the inner side of the proximal end region, a plurality of radially inwardly protruding cleats are provided for engaging behind each corresponding radially outwardly protruding cleat of the endoscope, wherein each radially inwardly protruding cleat is provided on an assigned section of the proximal end region that is elastically deformable in the axial direction of the outer shaft.

The plurality of radially inwardly protruding cleats and the plurality of elastically deformable sections are in particular equal to one another and distributed uniformly over a circumference of the proximal end region. In particular, two radially inwardly protruding cleats are provided on each elastically deformable section and are arranged opposite one another.

An endoscope system comprises an outer shaft, as it is described here, and an endoscope with a shaft, a proximal end region, a sealing surface corresponding to the sealing surface of the outer shaft on the proximal end region of the endoscope and a radially outwardly protruding cleat for engaging behind the radially inwardly protruding cleat on the inner side of the proximal end region of the outer shaft.

BRIEF DESCRIPTION OF THE FIGURES

Embodiments are explained in more detail below on the basis of the enclosed figures, in which is shown.

DESCRIPTION OF THE EMBODIMENTS

Figure 1:
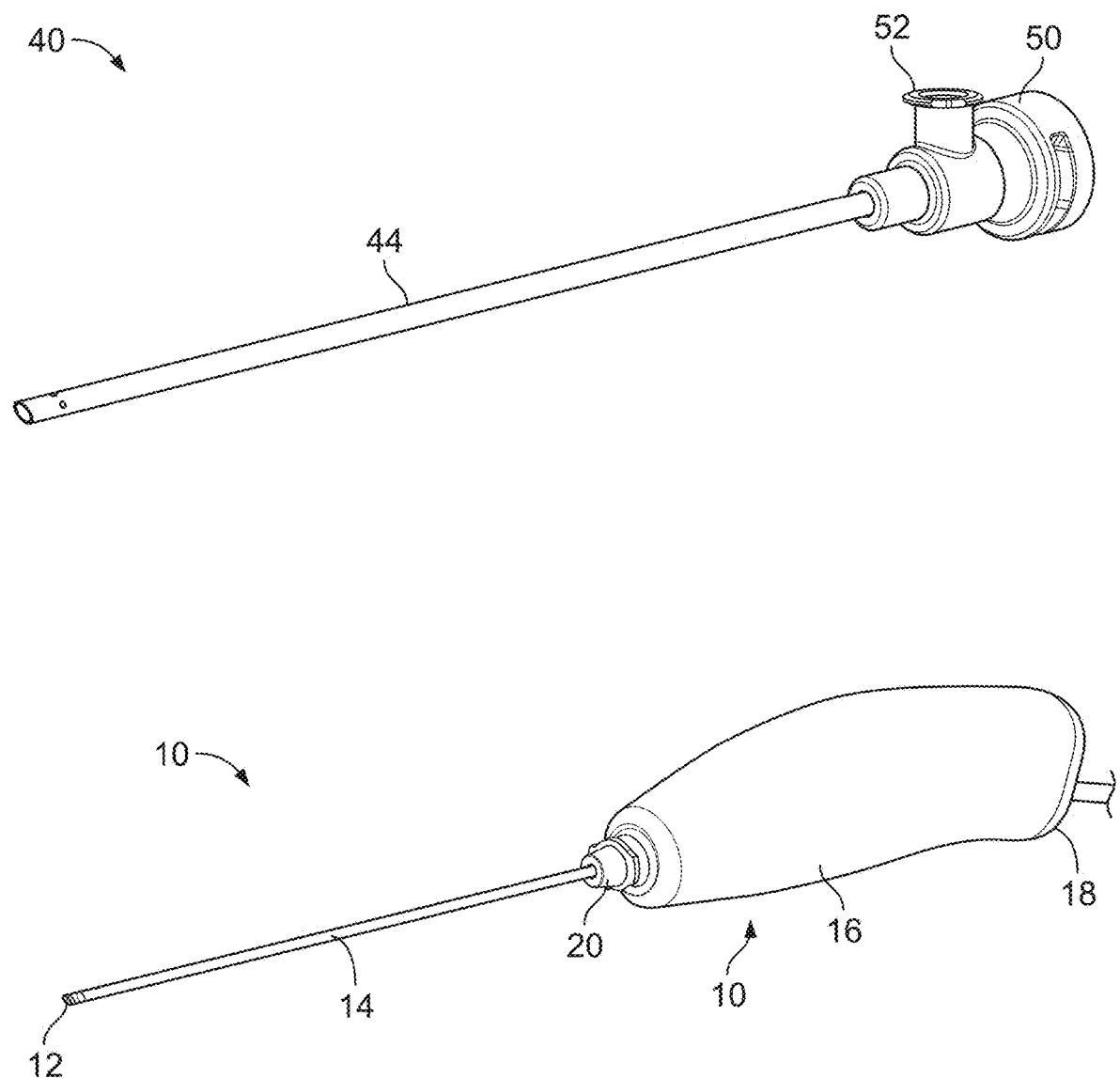
FIG. 1 a schematic axonometric illustration of an endoscope system.

FIG. 1 shows a schematic axonometric illustration of an endoscope system with an endoscope 10 and an outer shaft 40. The distal end 12 of the endoscope 10 is formed by a shaft 14 which is designed to be straight and rigid in the illustrated example. A handling device 16 forms the proximal end 18 of the endoscope 10. In a proximal end region 20 of the shaft 14, said shaft merges into the handling device 16.

The outer shaft 40 comprises a shaft tube 44 and a proximal end region 50 with a fluid connection 52, which is designed as a flushing connection in the illustrated example.

The cross-section of the lumen of the outer shaft, in particular of its shaft tube 44, is thus adapted to the cross-section of the shaft 14 of the endoscope such that the shaft 14 of the endoscope 10 can be fully inserted into the outer shaft 40 and its shaft tube 44 and a gap thereby remains between the outer surface of the shaft 14 of the endoscope 10 and the inner surface of the outer shaft 40. This gap has in particular a ring-shaped or a C-shaped cross-section and extends up to the distal end 12 of the endoscope 10. A flushing fluid can be channeled through the flushing connection 52 into the outer shaft 40, which flows through the gap up to the distal end 12 of the endoscope 10 and exits there.

Figure 2:
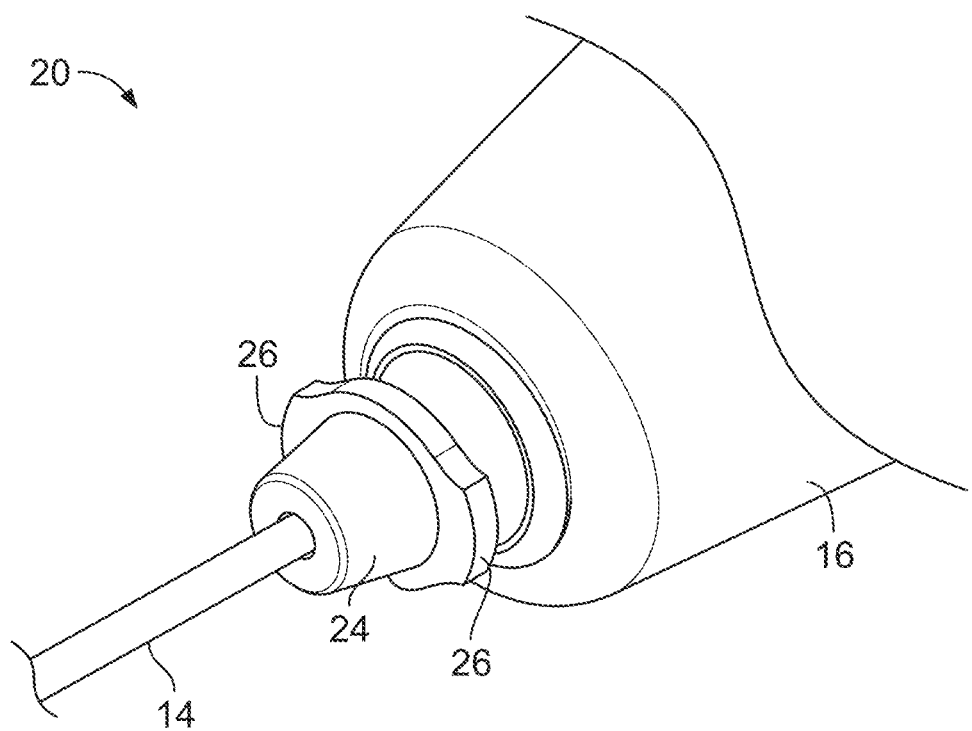
FIG. 2 a schematic axonometric illustration of an endoscope of the endoscope system from FIG. 1.

FIG. 2 shows an enlarged schematic axonometric illustration of a part of the endoscope 10 of the endoscope system from FIG. 1, namely of the proximal end region 20 of the shaft 14 and of the adjoining distal end of the handling device 16. In the proximal end region 20 of the shaft 14 of the endoscope 10, an outer cone 24 and, proximal to the outer cone 24, two cleats 26 are provided. The cleats 26 are provided on two sides of the proximal end region 20 facing away from one another. In the illustrated example, each cleat 26 has approximately the shape of a radially outwardly protruding web with rectangular cross-section. The outer contours of the cleats 26 are each in the shape of a circular arc and form sections of the same circle, whose middle point lies on the longitudinal and symmetry axis of the shaft 14.

Figure 3:
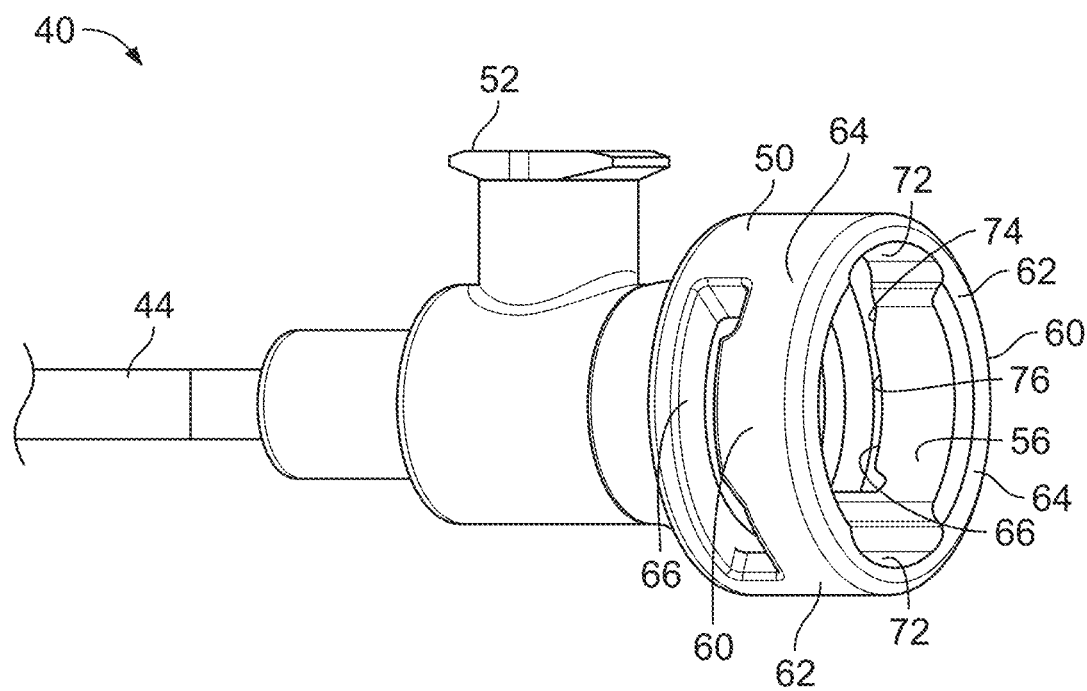
FIG. 3 a schematic axonometric illustration of a proximal end of an outer shaft of the endoscope system from FIG. 1.

FIG. 3 shows a schematic and enlarged axonometric illustration of the proximal end region 50 of the outer shaft of the endoscope system from FIG. 1. The proximal end region 50 of the outer shaft 40 is permanently and rigidly mechanically connected to the shaft tube 44 of the outer shaft 40. The outer shaft 40 can be formed monolithically, for example as a plastic injection-molded part, which comprises both the shaft tube 44 and the proximal end region 50. Alternatively, the shaft tube 44 can be joined to the proximal end region 50 of the outer shaft 40, for example by adhesion or welding. In this case, for example the shaft tube 44 is formed of metal and the proximal end region 50 of the outer shaft 40 is formed of plastic.

In the illustrated example, the flushing connection 52 is arranged radially. The flushing connection 52 can be designed as a Luer coupling.

The proximal end region 50 of the outer shaft 40 is designed in a cup shape and has two opposing, radially inwardly protruding cleats 56. In the illustrated example, the cleats 56 are designed with a large area, the depth of each cleat 56 measured in the direction parallel to the longitudinal axis of the outer shaft 40 and the width of each cleat 56 measured in the direction of the circumference is greater or notably greater than the height of each cleat 56 measured in the radial direction. Each cleat 56 is arranged on an elastically deformable section 60 of the proximal end region 50 of the outer shaft 40. Each elastically deformable section 60 has substantially the shape of a curved bar following the outer contour of the proximal end region 50 and is monolithically connected via its ends 62, 64 to the other proximal end region 50. Each slot 66 separates each elastically deformable section 60 from the other proximal end region 50. The ends of the slots 66 define the ends 62, 64 of the elastically deformable sections 60.

Radial depressions or recesses 72 are provided in the circumferential direction between the cleats 56. The cross-sections of the recesses 72 are adapted to the cross-sections of the cleats 26 on the proximal end region 20 of the endoscope 10 (see FIGS. 1, 2), wherein the cross-sections are regarded as sections in planes orthogonal to the longitudinal axis of the outer shaft 40. Therefore, after introducing the shaft 14 of the endoscope 10 (see FIGS. 1, 2) into the outer shaft 40, the cleats 26 on the proximal end region 20 of the endoscope 10 are moved in the axial direction through the recesses 72 until they are arranged in a plane with the slots 66.

In the case of a subsequent rotation of the outer shaft 40 relative to the endoscope 10, the cleats 26 on the proximal end region 20 of the endoscope 10 (see FIGS. 1, 2) slide along ramp surfaces 74 on the cleats 56 and further along plateau surfaces 76 on the cleats 56 in the proximal end region 50 of the outer shaft 40. If the cleats 26 on the proximal end region 20 of the endoscope 10 are arranged distal to the cleats 56 in the proximal end region 50 of the outer shaft 40, the outer shaft 40 is held in a positive-locking manner on the endoscope 10. When the cleats 26 on the proximal end region 20 of the endoscope 10 slide along the ramp surfaces 74 on the cleats 56, the elastically deformable sections 60 are elastically deformed, namely the cleats 56 are displaced proximally. Elastic restoring forces of the elastically deformable sections 60 press the cleats 56 from the proximal direction against the cleats 26 on the proximal end region 20 of the endoscope 10.

Figure 4:
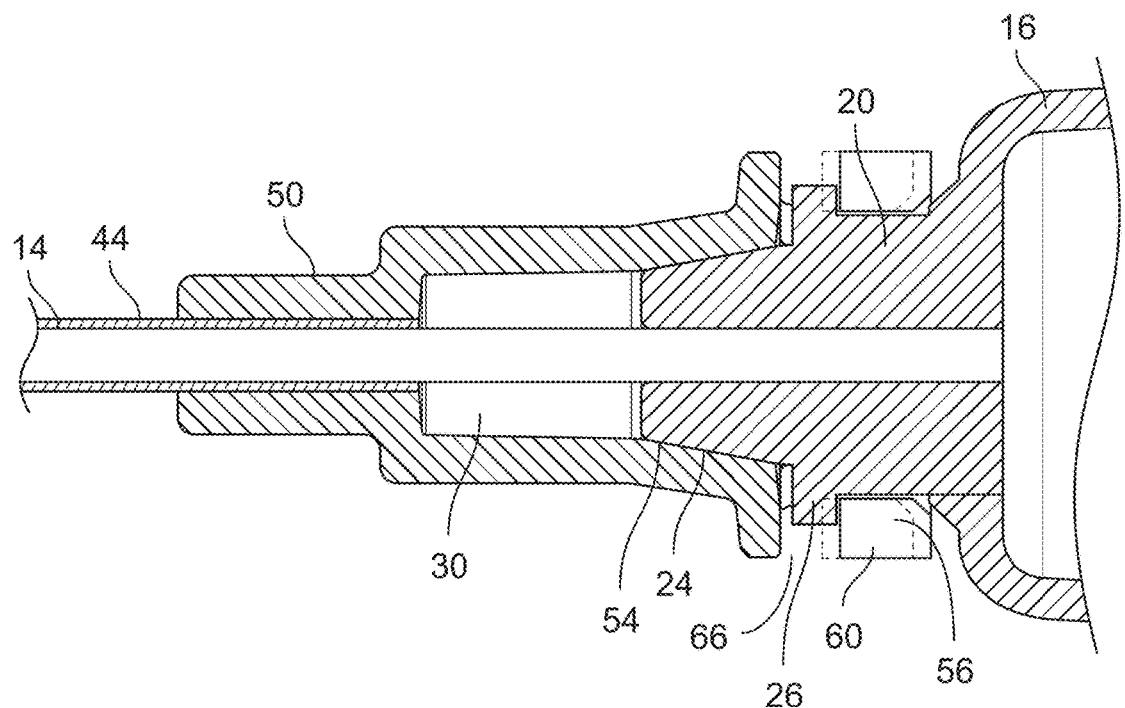
FIG. 4 a schematic illustration of a section through the endoscope system from FIGS. 1 to 3.

FIG. 4 shows a schematic illustration of a section through a part of the endoscope system from FIGS. 1 to 3, namely through the proximal end region 20 of the shaft 14 of the endoscope 10 and through the proximal end region 50 of the outer shaft 40. The section plane of FIG. 4 includes the longitudinal and symmetry axes of the shaft 14 of the endoscope 10 and of the shaft tube 44 of the outer shaft 40 and is orthogonal to the direction of extension of the flushing connection 52. The section plane of FIG. 4 intersects the cleats 26 on the proximal end region 20 of the shaft 14 of the endoscope 10 and the cleats 56 in the proximal end region 50 of the outer shaft 40.

The proximal end region 50 of the outer shaft 40 has an inner cone 54 corresponding to the outer cone 24 on the proximal end region 20 of the shaft 14 of the endoscope 10.

FIG. 4 shows the configuration intended for the use of the endoscope system, in which the cleats 26 on the proximal end region 20 of the shaft 14 of the endoscope 10 are arranged distally to the cleats 56 in the proximal end region 50 of the outer shaft 40. The elastically deformable sections 60 are elastically deformed, wherein they are displaced from their positions in a mechanically tension-free state indicated in FIG. 4 with dashed lines proximally into the positions illustrated in FIG. 4 with continuous lines. The resulting elastic restoring force presses the cleats 56 in the proximal end region 50 of the outer shaft 40 from the distal direction against the cleats 26 on the proximal end region 20 of the shaft 14 of the endoscope 10 and therefore also the outer cone 24 on the proximal end region 20 of the shaft 14 against the inner cone 54 in the proximal end region 50 of the outer shaft 40.

By inclining the surfaces of outer cone 24 and inner cone 54, the surface normal force between the same is increased compared to the elastic restoring force of the elastically deformable sections 60. The resulting friction, in particular the adhesive friction between the cleats 26, 56 and in particular between outer cone 24 and inner cone 54 prevents an unintended rotation of the outer shaft 40 relative to the endoscope 10 back to the configuration in which the cleats 26 on the proximal end region 20 of the shaft 14 of the endoscope 10 can be moved in the axial direction through the recesses 72 (see FIG. 3) out of the proximal end region 50 of the outer shaft 40.

In FIG. 4, the intermediate space 30 between the outer surface of the shaft 14 of the endoscope 10 and the inner surface of the outer shaft 40 is discernible. The intermediate space 30 extends with ring-shaped cross-section to the distal end 12 of the endoscope 10 (see FIG. 1). The proximal end of the intermediate space 30 is extended in a ring-shaped manner in the proximal end region 50 of the outer shaft 40. The outer cone 24 on the proximal end region 20 of the shaft 14 of the endoscope 10 and the inner cone 54 in the proximal end region 50 of the outer shaft 40 form sealing surfaces resting on one another which seal the intermediate space 30 proximally in a fluid-tight manner.

Figure 5:
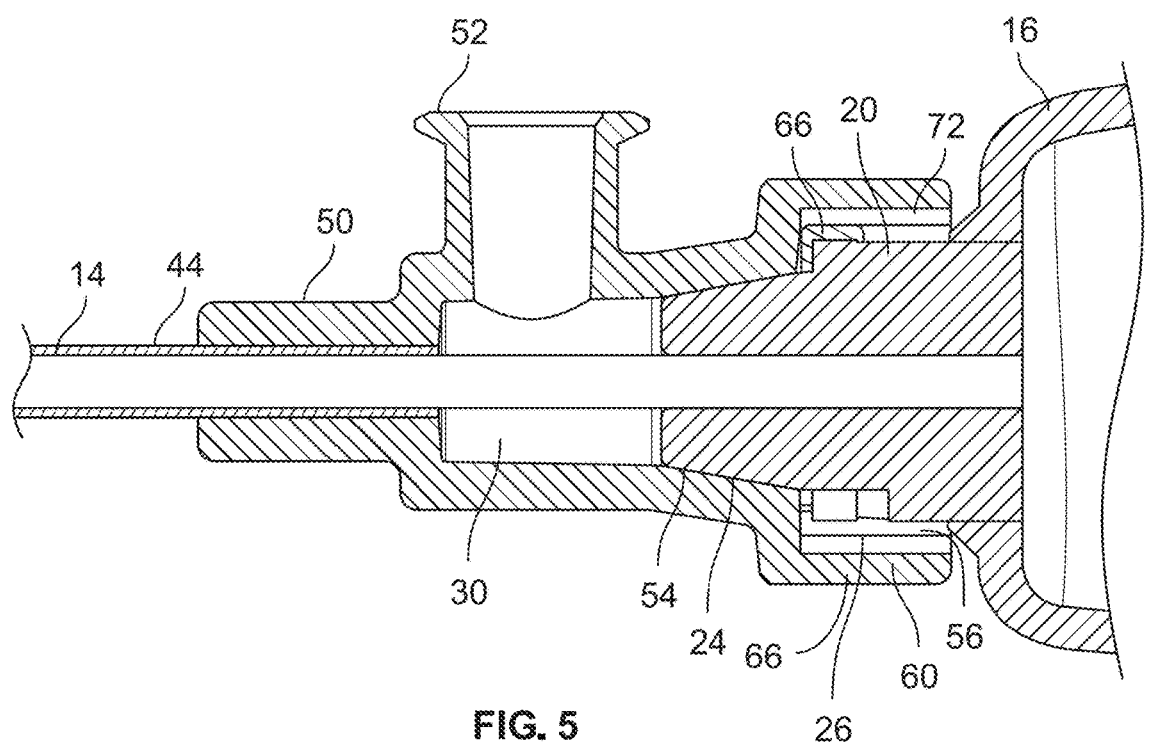
FIG. 5 a schematic illustration of a further section through the endoscope system from FIGS. 1 to 4.

FIG. 5 shows a schematic illustration of a further section through a part of the endoscope system from FIGS. 1 to 4, namely the proximal end region 20 of the shaft 14 of the endoscope 10 and the proximal end region 50 of the outer shaft 40. The section plane of FIG. 5 includes the longitudinal and symmetry axes of the shaft 14 of the endoscope 10 and of the shaft tube 44 of the outer shaft 40, is orthogonal to the section plane of FIG. 4 and includes the direction in which the flushing connection 52 extends. The section plane of FIG. 5 intersects the recesses 72 in the proximal end region 50 of the outer shaft 40.

Figure 6:
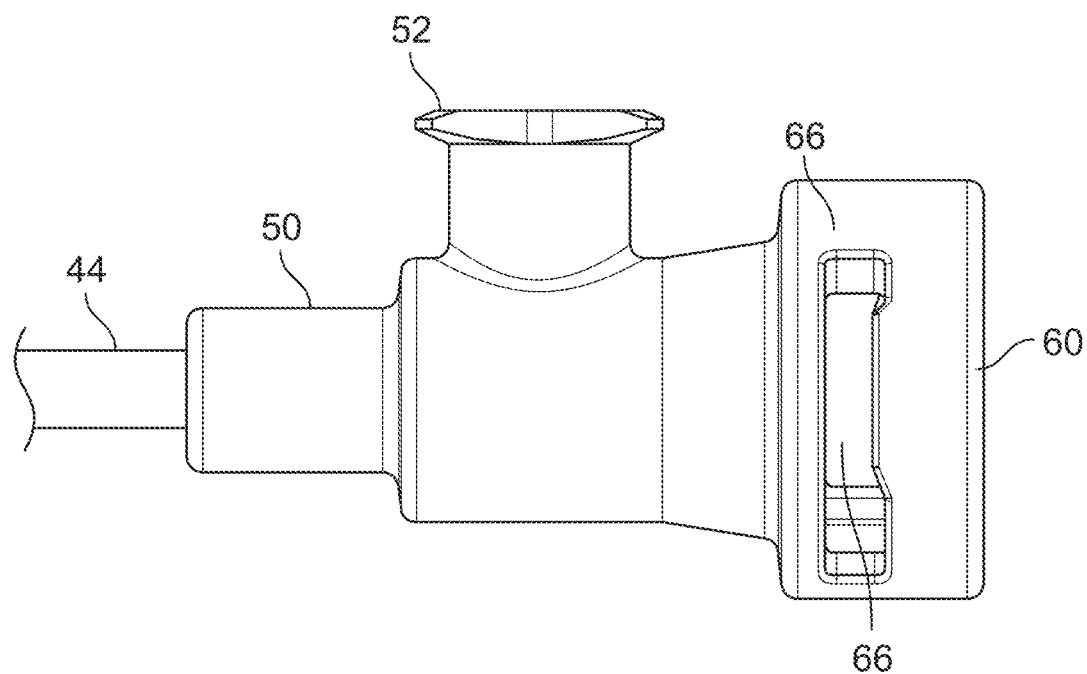
FIG. 6 a schematic illustration of the proximal end region of the outer shaft from FIGS. 1 and 3 to 5.

FIG. 6 shows a further schematic illustration of the proximal end region 50 of the outer shaft 40. The drawing plane of FIG. 6 is parallel to the section plane of FIG. 5.

The two slots 66 partially overlap in FIG. 6.

Figure 7:
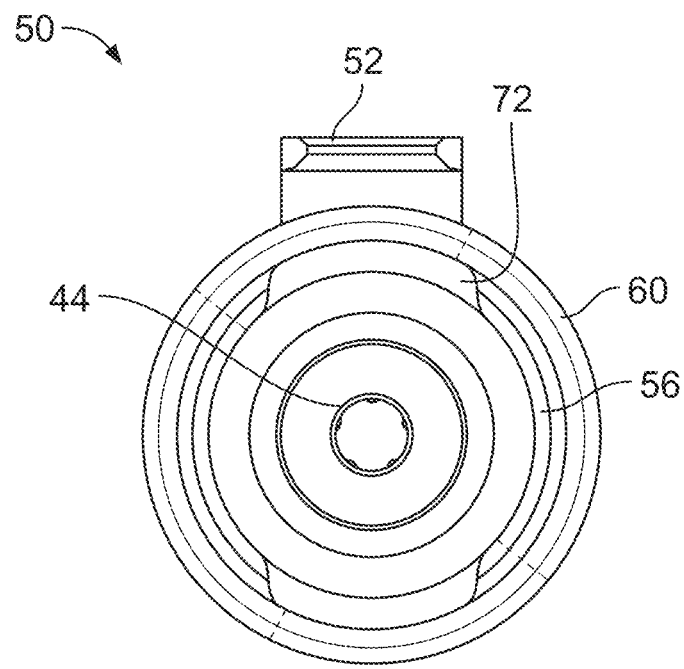
FIG. 7 a further schematic illustration of the proximal end region of the outer shaft from FIGS. 1 and 3 to 6.

FIG. 7 shows a further schematic illustration of the proximal end region 50 of the outer shaft 40 from FIGS. 1 and 3 to 6. The section plane of FIG. 7 is orthogonal to the section planes of FIGS. 4 and 5 and to the drawing plane of FIG. 6 and orthogonal to the longitudinal and symmetry axis of the outer shaft 40.

The cross-sections of the recesses 72 adapted to the shape of the cleats 26 on the proximal end region of the shaft 14 of the endoscope 10 (see FIGS. 1, 2, 4, 5) and the cleats 56 protruding inwardly between the recesses 72 are discernible, the slots 66 (see FIGS. 3, 4, 6) are not visible, but their ends are indicated with dashed lines.

REFERENCE NUMERALS

10 Endoscope
12 Distal end of the endoscope 10
14 Shaft of the endoscope 10
16 Handling device of the endoscope 10
18 Proximal end of the endoscope 10
20 Proximal end region of the shaft 14 of the endoscope 10
24 Outer cone on the proximal end region 20 of the shaft 14
26 Cleat on the proximal end region 20 of the shaft 14 of the endoscope 10
30 Intermediate space between the shaft 14 of the endoscope 10 and the outer shaft 40
40 Outer shaft for the endoscope 10
44 Shaft tube of the outer shaft 40
50 Proximal end region of the outer shaft 40
52 Flushing connection on the proximal end region 50
54 Inner cone in the proximal end region 50 of the outer shaft 40
56 Cleat in the proximal end region 50 of the outer shaft 40
60 Elastically deformable section of the proximal end region 50 of the outer shaft 40
62 First end of the elastically deformable section 60
64 Second end of the elastically deformable section 60
66 Slot in the proximal end region 50 of the outer shaft 40
72 Recess in the proximal end region 50 of the outer shaft 40
74 Ramp surface on the cleat 56
76 Plateau surface on the cleat 56

What is claimed is:

1. An outer shaft for receiving a shaft of an endoscope comprising:
   a proximal end region for receiving a proximal end region of the shaft of the endoscope;
   a sealing surface for resting on a corresponding sealing surface of the endoscope for locally fluid-tight sealing of an intermediate space between outer shaft and shaft of the endoscope; and
   a radially inwardly protruding cleat in the proximal end region for proximally and elastically engaging behind a radially outwardly protruding cleat on the proximal end region of the shaft of the endoscope,
   wherein the radially inwardly protruding cleat is provided on a section of the proximal end region of the outer shaft and is elastically deformable behind the radially outwardly protruding cleat in the axial direction of the outer shaft to elastically press the radially inwardly protruding cleat against the radially outwardly protruding cleat and to thereby elastically press the sealing surface of the endoscope against the sealing surface of the outer shaft.

2. The outer shaft according to claim 1, in which the elastically deformable section of the proximal end region has substantially the shape of a straight or curved bar, which is connected at one end or at both its ends to the other proximal end region.

3. The outer shaft according to claim 2, in which both ends of the elastically deformable section are connected to the other proximal end region of the outer shaft, the elastically deformable section has, close to its ends, an increased elastic flexibility.

4. The outer shaft according to claim 2, in which the elastically deformable section has, close to both its ends, reduced cross-sections.

5. The outer shaft according to claim 1, in which the elastically deformable section is separated from the other proximal end region by a slot running substantially in the circumferential direction of the proximal end region of the outer shaft.

6. The outer shaft according to claim 1, in which the proximal end region has a recess, which runs in the axial direction and is open radially inwardly, for passing through the radially outwardly protruding cleat on the proximal end region of the shaft of the endoscope while the shaft of the endoscope is inserted axially into the outer shaft, the radially inwardly protruding cleat of the outer shaft is designed and arranged in order to adopt in a sliding manner a position proximal to the radially outwardly protruding cleat of the endoscope during a rotation of the outer shaft, which follows the axial insertion, relative to the endoscope on the radially outwardly protruding cleat of the endoscope.

7. The outer shaft according to claim 1, further comprising:
a ramp surface on the cleat of the outer shaft for generating a force deforming the elastically deformable section in the axial direction of the outer shaft during a rotation of the outer shaft relative to the endoscope.

8. The outer shaft according to claim 1, in which in a configuration in which the outer shaft is connected to the endoscope in the intended manner, the elastic restoring force of the elastically deformable section presses the radially inwardly protruding cleat of the outer shaft in the axial direction against the radially outwardly protruding cleat of the endoscope and presses the sealing surface of the outer shaft against the corresponding sealing surface of the endoscope and thus locks the outer shaft in regard to a rotation relative to the endoscope in a frictionally-engaging manner.

9. The outer shaft according to claim 1, in which the outer shaft including the radially inwardly protruding cleat, is made of plastic and is intended and designed for single use.

10. The outer shaft according to claim 1, wherein the proximal end region defines an inner side, wherein on the inner side of the proximal end region a plurality of radially inwardly protruding cleats are provided for engaging behind each corresponding radially outwardly protruding cleat of the endoscope, wherein each radially inwardly protruding cleat is provided on an assigned section of the proximal end region that is elastically deformable in the axial direction of the outer shaft.

11. An endoscope system comprising:
an outer shaft according to claim 1;
an endoscope with a shaft, a proximal end region defining an inner side, a sealing surface corresponding to the sealing surface of the outer shaft on the proximal end region, a radially outwardly protruding cleat for engaging behind the radially inwardly protruding cleat on the inner side of the proximal end region of the outer shaft.

* * * * *